United States Patent

(12) United States Patent
Shiku et al.

(10) Patent No.: US 11,039,908 B2
(45) Date of Patent: Jun. 22, 2021

US011039908B2

(54) NEEDLELESS SYRINGE AND METHOD FOR INTRODUCING DNA INTO INJECTION TARGET AREA USING SAME

(71) Applicants: MIE UNIVERSITY, Mie (JP); DAICEL CORPORATION, Osaka (JP)

(72) Inventors: Hiroshi Shiku, Mie (JP); Yuzo Yamamoto, Hyogo (JP); Takaya Masumoto, Hyogo (JP)

(73) Assignees: MIE UNIVERSITY, Mie (JP); DAICEL CORPORATION, Osaka (JP)

( * ) Notice: Subject to any disclaimer, the term of this patent is extended or adjusted under 35 U.S.C. 154(b) by 671 days.

(21) Appl. No.: 15/737,268

(22) PCT Filed: Jun. 15, 2016

(86) PCT No.: PCT/JP2016/067825
§ 371 (c)(1),
(2) Date: Dec. 15, 2017

(87) PCT Pub. No.: WO2016/204184
PCT Pub. Date: Dec. 22, 2016

(65) Prior Publication Data

US 2018/0168789 A1 Jun. 21, 2018

(30) Foreign Application Priority Data

Jun. 16, 2015 (JP) ............................ JP2015-121046

(51) Int. Cl.
*A61D 1/02* (2006.01)
*A61D 7/00* (2006.01)
(Continued)

(52) U.S. Cl.
CPC ............... *A61D 1/025* (2013.01); *A61D 7/00* (2013.01); *A61K 9/0019* (2013.01);
(Continued)

(58) Field of Classification Search
CPC .......... A61M 5/2046; A61M 5/30–2005/3022; A61D 1/025; A61D 7/00;
(Continued)

(56) References Cited

U.S. PATENT DOCUMENTS

| | | |
|---|---|---|
| 4,124,024 A | 11/1978 | Schwebel et al. |
| 5,399,163 A | 3/1995 | Peterson et al. |

(Continued)

FOREIGN PATENT DOCUMENTS

| | | |
|---|---|---|
| EP | 2620175 * | 7/2013 |
| EP | 2620175 A1 | 7/2013 |

(Continued)

OTHER PUBLICATIONS

Gnjatic, et al. NY-ESO-1: Review of an Immunogenic Tumor Antigen, Feb. 2006, Advances in Cancer Research, pp. 1-30 (Year: 2006).*

(Continued)

*Primary Examiner* — Theodore J Stigell
*Assistant Examiner* — Daniel Moore
(74) *Attorney, Agent, or Firm* — Knobbe Martens Olson & Bear LLP

(57) ABSTRACT

A needleless injector which can selectively induce the immune response and a method for introducing DNA including a region coding for an antigen to selectively produce an antibody in a living body of a mammal by using the needleless injector are provided. Disclosed is a needleless injector for injecting a DNA solution into an injection target area without using any injection needles. The needleless injector includes an accommodating unit which accommo-
(Continued)

dates the DNA solution, a predetermined ignition device; and a predetermined nozzle unit. A temperature of the predetermined combustion product, which is provided during the pressurization, changes to a neighborhood of ordinary temperature within 20 msec after a pressure, which is applied to the DNA solution on account of the combustion of the igniter powder, reaches an initial peak discharge force during a pressurization process for discharging the DNA solution.

7 Claims, 10 Drawing Sheets

(51) Int. Cl.

| | |
|---|---|
| ***A61K 39/00*** | (2006.01) |
| ***A61K 31/7088*** | (2006.01) |
| ***A61M 5/20*** | (2006.01) |
| ***A61M 5/30*** | (2006.01) |
| ***A61K 9/00*** | (2006.01) |

(52) U.S. Cl.
CPC .......... *A61K 31/7088* (2013.01); *A61K 39/00* (2013.01); *A61K 39/0011* (2013.01); *A61K 39/001188* (2018.08); *A61M 5/2046* (2013.01); *A61M 5/30* (2013.01); *A61K 2039/51* (2013.01); *A61K 2039/53* (2013.01); *A61K 2039/54* (2013.01); *A61K 2039/552* (2013.01)

(58) Field of Classification Search
CPC ............ A61K 39/001188; A61K 39/00; A61K 31/7088; A61K 9/0019; A61K 39/0011; A61K 2039/51; A61K 2039/53; A61K 2039/54; A61K 2039/552; A61P 35/00
See application file for complete search history.

(56) References Cited

U.S. PATENT DOCUMENTS

| | | | | |
|---|---|---|---|---|
| 5,584,807 | A * | 12/1996 | McCabe | A61M 5/3015 604/24 |
| 6,936,303 | B1 | 8/2005 | Katsuda et al. | |
| 2002/0174792 | A1 | 11/2002 | Kubozuka et al. | |
| 2004/0049151 | A1 | 3/2004 | Lell | |
| 2005/0010168 | A1 | 1/2005 | Kendall | |
| 2009/0212125 | A1* | 8/2009 | McIntosh | A61M 11/041 239/88 |
| 2014/0200512 | A1 | 7/2014 | Oda | |
| 2015/0032082 | A1 | 1/2015 | Kudoh | |
| 2016/0367651 | A1 | 12/2016 | Shiku et al. | |

FOREIGN PATENT DOCUMENTS

| | | | |
|---|---|---|---|
| JP | S51-046792 | A | 4/1976 |
| JP | 2002-511396 | A | 4/2002 |
| JP | 2003-025950 | A | 1/2003 |
| JP | 2004-500933 | A | 1/2004 |
| JP | 2004-358234 | A | 12/2004 |
| JP | 2005-021640 | A | 1/2005 |
| JP | 2012-065922 | A | 4/2012 |
| JP | 2014-176759 | A | 9/2014 |
| WO | WO 99/052463 | A1 | 10/1999 |
| WO | WO 01/031282 | A1 | 5/2001 |
| WO | WO 2012/006378 | A1 | 1/2012 |
| WO | WO 2015/050158 | A1 | 4/2015 |

OTHER PUBLICATIONS

International Search Report dated Sep. 13, 2016 in International Application No. PCT/JP2016/067825.
Office Action dated Oct. 17, 2018 in corresponding Russian Application No. 2018101198.
International Preliminary Report on Patentability dated Dec. 19, 2017 in International Application No. PCT/JP2016/067825.
Extended European Search Report dated Nov. 26, 2018 in related European Application No. 16811658.0.

* cited by examiner

NEEDLELESS SYRINGE AND METHOD FOR INTRODUCING DNA INTO INJECTION TARGET AREA USING SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present invention relates to a needleless injector and a method for introducing DNA based on the use of the same.

BACKGROUND ART

In the case of a needleless injector which performs the injection without using any injection needle, such a structure is sometimes adopted that an injection component is discharged by applying the pressure to an accommodating chamber in which an injection solution is accommodated, by means of a pressurized gas or a spring.

For example, in the case of a needleless injector described in Patent Literature 1, the following structure is adopted. That is, a plurality of nozzle holes are formed at the inside of a main injector body, and a piston, which is to be driven upon the discharge, is arranged corresponding to each of the nozzle holes.

Based on this structure, it is intended to realize the uniform injection with respect to a target by simultaneously jetting an injection solution from the plurality of nozzle holes.

Further, such a form is known that a pressurized gas is utilized as a power source for discharging an injection solution by using a needleless injector. For example, in the case of needleless injectors described in Patent Literatures 2 and 3, such a pressurization form is exemplified that the pressurization is instantaneously performed to a great extent at the initial stage of the discharge, and then the pressurizing force is gradually reduced over 40 to 50 msec.

On the other hand, Patent Literature 4 describes a method for inducing the immune response with respect to a protein antigen to be expressed in vivo by using a needleless emission type injection apparatus in order to administer DNA, a DNA preparation, and/or other polynucleotide for performing genetic vaccine inoculation, gene transport, and gene therapy.

Specifically, a method is described, in which the immune response with respect to a polynucleotide vaccine is induced in animal by using a needleless injector (produced by BIOJECTOR (trade name)). Further, in an exemplary embodiment thereof, it is described that when a DNA vaccine was introduced into muscle of a test animal by using the needleless injector, the immune response was exhibited, which was more significant as compared with a case of use of a needle-equipped injector.

However, in the immune response, any antibody, which is unfavorable to be induced, is produced in some cases. Any DNA and any DNA preparation and any method for introducing the same into the living body are not known, in which the antibody the production of which is favorable to be induced is produced while the antibody the production of which is unfavorable to be induced is not produced.

CITATION LIST

Patent Literatures

Patent Literature 1: Japanese Patent Application Laid-Open No. 2004-358234

Patent Literature 2: U.S. Pat. No. 5,399,163

Patent Literature 3: United States Patent Application Publication No. 2005/0010168

Patent Literature 4: Japanese Patent Application Laid-Open No. 2002-511396 (PCT)

SUMMARY OF THE INVENTION

Problems to be Solved by the Invention

The present invention has been made in the circumstances as described above, an object of which is to provide such a needleless injector that an antibody the production of which is favorable to be induced is produced while an antibody the production of which is unfavorable to be induced is not produced, i.e., a needleless injector which can selectively induce the immune response, and a method for introducing DNA including a region coding for an antigen to selectively produce an antibody into a living body of a mammal by using the needleless injector.

Means for Solving the Problems

As a result of diligent investigations, the present inventors have found out that a needleless injector described below can achieve the foregoing object, as a result of the attention given to the characteristic of a combustion product brought about by an igniter powder as well as the pressure applied to a DNA solution by ignition and the temperature of the combustion product by using an ignition device based on the use of the igniter powder for the needleless injector, and thus the present inventors have completed the present invention. The present invention is as follows.

<1> A needleless injector for injecting a DNA solution into an injection target area without using any injection needle, the needleless injector comprising:

an accommodating unit which accommodates the DNA solution;

an ignition device including an igniter powder which exhibits such a pressure characteristic that a plasma is generated during combustion immediately after ignition and then a generated pressure is lowered when a temperature becomes ordinary temperature and a combustion product is condensed on account of no gas component which is contained in the combustion product or any gas component which is contained in the combustion product and an amount of which is decreased as compared with that provided before the condensation; and a nozzle unit having a discharge port through which the DNA solution pressurized by the combustion of the igniter powder in the ignition device flows so that the DNA solution is discharged to the injection target area, wherein:

a temperature of the combustion product, which is provided during the pressurization, changes to a neighborhood of the ordinary temperature within 20 msec after a pressure, which is applied to the DNA solution on account of the combustion of the igniter powder, reaches an initial peak discharge force during a pressurization process for discharging the DNA solution.

<2> The needleless injector according to <1>, wherein the temperature of the combustion product, which is provided during the pressurization, changes to the neighborhood of the ordinary temperature within 10 msec after the pressure, which is applied to the DNA solution on account of the combustion of the igniter powder, reaches the initial peak discharge force.

<3> A method for introducing DNA including a region coding for an antigen into a living body of a mammal (except for human) by using the needleless injector as defined in <1> or <2>.

<4> The method according to <3>, wherein the DNA is in a form of vaccine.

<5> The method according to <3> or <4>, wherein the mammal (except for human) is mouse.

<6> The method according to any one of <3> to <5>, wherein the antigen is NY-ESO-1 antigen.

Advantageous Effect of the Invention

According to the present invention, it is possible to provide the needleless injector which can selectively induce the immune response, and the method for introducing DNA including a region coding for an antigen to selectively produce an antibody in a living body of a mammal by using the needleless injector.

EMBODIMENTS FOR CARRYING OUT THE INVENTION

Figure 1:
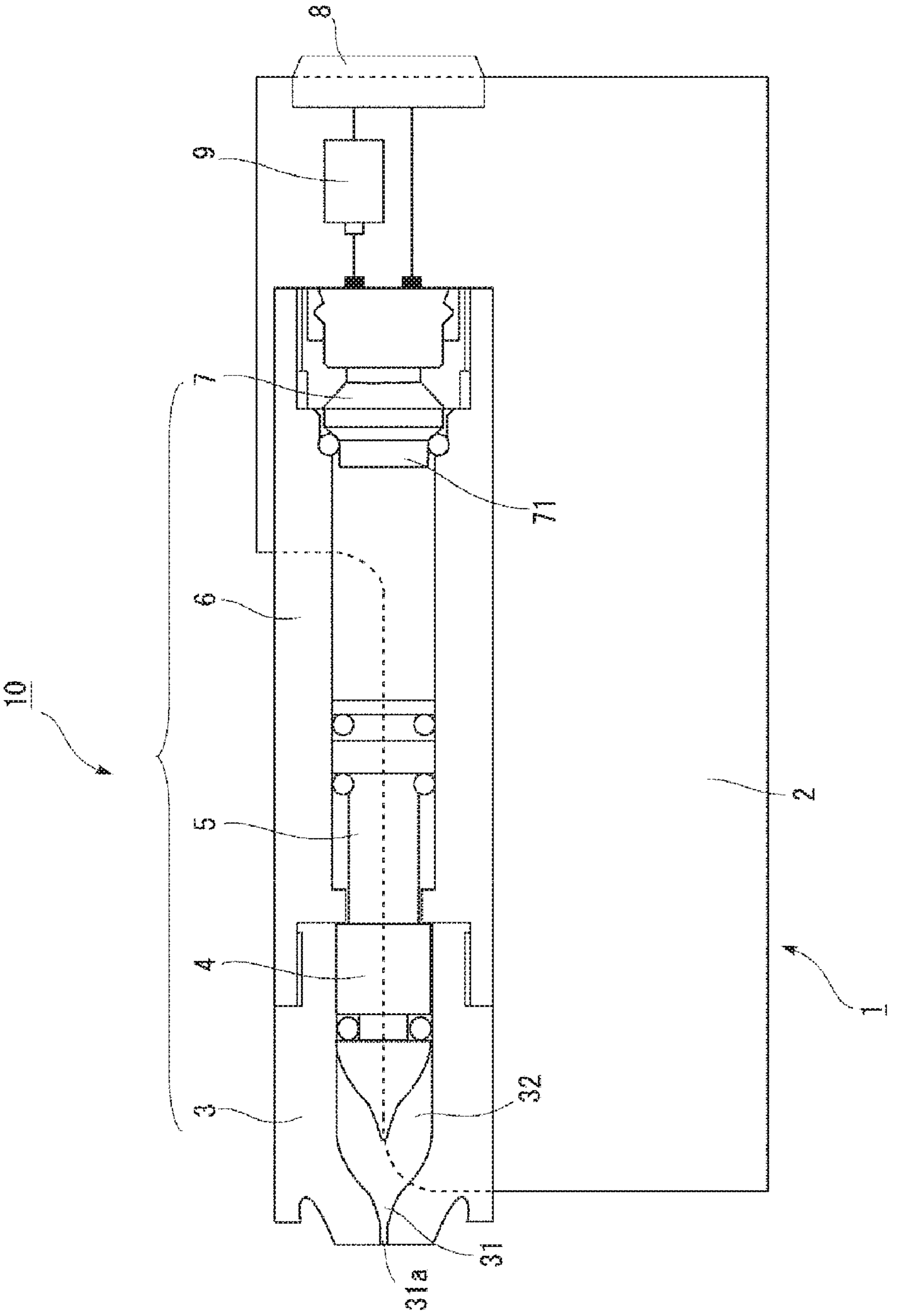
FIG. 1 shows a schematic arrangement of an injector according to the first invention of the present invention.

The present invention includes the first invention which relates to the invention of the needleless injector, and the second invention which relates to the invention of the method for introducing DNA including a region coding for an antigen into a living body of a mammal (except for human) by using the needleless injector.

<First Invention>

The first invention of the present invention resides in a needleless injector for injecting a DNA solution into an injection target area without using any injection needle; the needleless injector comprising an accommodating unit which accommodates the DNA solution; an ignition device including an igniter powder which exhibits such a pressure characteristic that a plasma is generated during combustion immediately after ignition and then a generated pressure is lowered when a temperature becomes ordinary temperature and a combustion product is condensed on account of no gas component which is contained in the combustion product or any gas component which is contained in the combustion product and an amount of which is decreased as compared with that provided before the condensation; and a nozzle unit having a discharge port through which the DNA solution pressurized by the combustion of the igniter powder in the ignition device flows so that the DNA solution is discharged to the injection target area; wherein a temperature of the combustion product, which is provided during the pressurization, changes to a neighborhood of the ordinary temperature within 20 msec after a pressure, which is applied to the DNA solution on account of the combustion of the igniter powder, reaches an initial peak discharge force during a pressurization process for discharging the DNA solution.

In the injector according to the first invention of the present invention, the term "forward end side" means the side on which the discharge port for discharging the injection objective substance from the injector is arranged, and the term "proximal end side" means the side which is opposite to the forward end side. These terms do not refer to any specified place or any specified position in any limited manner.

In the injector according to the first invention of the present invention, the driving unit adopts, as the discharge energy, the combustion energy of the propellant or explosive ignited by the ignition device. Note that when the combustion energy of the propellant is utilized as the discharge energy, for example, the propellant may be any one propellant of a propellant containing zirconium and potassium perchlorate (ZPP), a propellant containing titanium hydride and potassium perchlorate (THPP), a propellant containing titanium and potassium perchlorate (TiPP), a propellant containing aluminum and potassium perchlorate (APP), a propellant containing aluminum and bismuth oxide (ABO), a propellant containing aluminum and molybdenum oxide (AMO), a propellant containing aluminum and copper oxide (ACO), and a propellant containing aluminum and iron oxide (AFO), or a propellant composed of a combination of a plurality of the foregoing propellants. The feature of these propellants is as follows. That is, the combustion product thereof does not contain the gas component at the ordinary temperature even when the combustion product is the gas in a high temperature state. Therefore, the combustion product immediately performs the condensation after the ignition. Accordingly, the temperature of the combustion product, which is provided during the pressurization, can be allowed to change to the neighborhood of the ordinary temperature in a short period of time after the pressure, which is applied to the DNA solution on account of the combustion of the igniter powder, reaches the initial peak discharge pressure, during the pressurization process for discharging the DNA solution. The time (period of time) is usually within 20 msec and preferably within 10 msec. As a result, as described later on, when DNA including the region coding for the antigen is introduced into the living body, it is possible to selectively induce the immune response. Further, when the energy generated by the gas producing agent is utilized as the discharge energy, it is also possible to use, as the gas producing agent, a single base smokeless propellant and a variety of gas producing agents used for a gas generator for the air bag and a gas generator for the seat belt pretensioner.

The discharge energy, which is brought about by the driving unit, is transmitted via a piston to a plunger, and the plunger slides in a charging chamber. Accordingly, the DNA solution, which is accommodated in the charging chamber, is extruded along a flow passage formed in the nozzle unit. The DNA solution is finally discharged from the discharge port to the injection target area.

In this context, in the case of the injector according to the first invention of the present invention, the DNA solution is not accommodated in the charging chamber from the beginning. The DNA solution is accommodated by sucking the DNA solution into the charging chamber by the aid of a nozzle having the discharge port. In this way, the structure, which requires the charging operation for performing the charging into the charging chamber, is adopted.

Accordingly, it is possible to inject any arbitrary DNA solution which is required. On this account, in the case of the injector according to the first invention of the present invention, the syringe unit and the main injector body are constructed detachably.

An explanation will be made below with reference to the drawing about an injector 1 according to a first embodiment of the first invention of the present invention. The structure or construction of the following embodiment is provided by way of example, and the first invention of the present invention is not limited to the structure or construction of this embodiment. Note that the "forward end side" and the "proximal end side" are used as the terms to represent the relative positional relationship in the longitudinal direction of the injector 1. The "forward end side" represents the position which is deviated toward the forward end of the injector 1 as described later on, i.e., deviated toward the discharge port 31*a*. The "proximal end side" represents the direction opposite to the "forward end side" in the longitudinal direction of the injector 1, i.e., the direction on the side of the driving unit 7.

(Structure of Injector 1)

FIG. 1 shows a schematic structure of the injector 1, illustrating a sectional view taken along the longitudinal direction of the injector 1 as well. The injector 1 is constructed such that an injector assembly 10, which is obtained by integrally assembling a sub-assembly constructed by a syringe unit 3 and a plunger 4 and a sub-assembly constructed by a main injector body 6, a piston 5, and a driving unit 7, is attached to a housing (injector housing) 2.

As described above, the injector assembly 10 is constructed so that the injector assembly 10 is detachable with respect to the housing 2. The DNA solution is charged into a charging chamber 32 which is formed between the syringe unit 3 and the plunger 4 included in the injector assembly 10. Then, the injector assembly 10 is a unit which is used once and thrown away every time when the DNA solution is discharged. On the other hand, a battery 9, which supplies the electric power to an igniter 71 included in the driving unit 7 of the injector assembly 10, is included in the part of the housing 2. The electric power is supplied from the battery 9 via the wiring between the electrode disposed on the side of the housing 2 and the electrode disposed on the side of the driving unit 7 of the injector assembly 10, in accordance with the operation performed by a user to depress a button 8 provided on the housing 2. Note that as for the electrode disposed on the side of the housing 2 and the electrode disposed on the side of the driving unit 7 of the injector assembly 10, the shapes and the positions of the both electrodes are designed so that the both electrodes are automatically brought in contact with each other when the injector assembly 10 is attached to the housing 2. Further, the housing 2 is a unit which can be repeatedly used as long as the electric power, which can be supplied to the driving unit 7, remains in the battery 9. Note that as for the housing 2, when the electric power of the battery 9 is exhausted, then only the battery 9 may be exchanged, and the housing 2 may be continuously used.

Further, any additional propellant component is not specifically arranged in the main injector body 6 shown in FIG. 1. However, in order to adjust the transition or change of the pressure applied to the injection solution by the aid of the piston 5, a gas producing agent or the like, which produces the gas by being combusted by the combustion product produced by the combustion of the propellant in the igniter 71, can be also arranged in the igniter 71 or in a through-hole of the main injector body 6. The structure, in which the gas producing agent is arranged in the igniter 71, resides in an already known technique as disclosed, for example, in International Publication No. 01-031282 and Japanese Patent Application Laid-Open No. 2003-25950. Further, an example of the gas producing agent is exemplified by a single base smokeless propellant composed of 98% by mass of nitrocellulose, 0.8% by mass of diphenylamine, and 1.2% by mass of potassium sulfate. Further, it is also possible to use a variety of gas producing agents used for a gas generator for the air bag and a gas generator for the seat belt pretensioner. It is possible to change the combustion completion time of the gas producing agent by adjusting the dimension, the size, and the shape, especially the surface shape of the gas producing agent arranged in the through-hole. Accordingly, the pressure transition to be applied to the injection solution can be a desired transition, i.e., a transition with which the injection solution can appropriately arrive at the injection target area. In the first invention of the present invention, the gas producing agent or the like, which is optionally used, is also included in the driving unit 7.

<Second Invention>

The second invention of the present invention resides in a method for introducing DNA including a region coding for an antigen into a living body of a mammal (except for human) by using the needleless injector of the first invention.

(Antibody)

As mentioned in Examples described later on, when the introducing method is carried out, then the antibody, the production of which is favorable to be induced, is thereby produced, while the antibody, the production of which is unfavorable to be induced, is not produced. That is, it is possible to selectively induce the immune response. The type, the subtype and the like of the antibody as described above are not specifically limited respectively. However, in this case, an explanation will be made as exemplified by IgG1 antibody and IgG2 antibody by way of example.

It is known that 0-type helper T cells (Th0 cells), which are precursor cells of helper T cells, are differentiated into Type 1 helper T cells (Th1 cells) or Type 2 helper T cells (Th2 cells), Th1 cells facilitate the cellular immunity, and Th2 cells facilitate the humoral immunity. The immune system is established by the balance between Th1 cells and Th2 cells.

Th1 cells participate in the activation of cytotoxic T cells (killer T cells, CTL), which have the protection from infection and the immune effect on cancer cells. On this account, the immunotherapy against cancer cells, which uses Th1 cells, is also developed. However, if Th1 cells are superior, and Th2 cells are inferior, then the autoimmune disease, in which autologous cells are also attacked, is caused.

On the other hand, Th2 cells especially participate in B cells which produce the antibody. Th2 cells can exhibit the immune effect in a broad range in the living body. However, Th2 cells also participate in the allergic inflammation, and Th2 cells secrete various interleukins. As a result, B cells are differentiated into IgE antibody producing cells, and/or B cells facilitate the degranulation and the activation of eosinophile. It is known that B cells thereby cause allergic diseases including, for example, atopic asthma and allergic rhinitis. On this account, it is not preferable that Th1 cells are inferior and Th2 cells are superior.

As described above, in the living body, the state, in which one of Th1 cells and Th2 cells is superior, is not unfavorable, and it is favorable that the balance is given. However, in the case of the cancer therapy, it is favorable that Th1 cells are superior and Th2 cells are inferior as even the cancer therapy has been developed as described above.

The superiority/inferiority can be judged by measuring the antibody titers for the antibodies in which respective cells specifically participate in the process until the production of the antibodies. The types of the antibodies, in relation to which respective cells specifically participate in the production, are known.

However, for example, it is known that Th1 cells participate in the production of IgG2 antibody (which may be, for example, IgG2a antibody belonging to a subclass thereof), and Th2 cells participate in the production of IgG1 antibody. Therefore, in the cancer therapy in which it is preferable that Th1 cells are superior and Th2 cells are inferior, it is preferable that IgG2 antibody is detected, and IgG1 antibody is not detected, or IgG1 antibody is not in an effective amount even if IgG1 antibody is detected.

Any known method, which includes, for example, ELISA method, is exemplified as the method for detecting the antibody. This will be briefly explained below. At first, a purified or partially purified antigen is adsorbed to the solid phase surface of 96-well plate for ELISA or the like, and the solid phase surface, to which the antigen is not adsorbed, is coated with a protein irrelevant to the antigen, for example, bovine serum albumin (hereinafter referred to as "BSA"). After washing the surface, the surface is brought in contact with a sample subjected to the dilution in a stepwise manner as a first antibody, and the monoclonal antibody contained in the sample is bound to the antigen. Further, an enzyme-labeled antibody against the mouse antibody is added as a second antibody so that the antibody is bound to the mouse antibody. After the washing, a substrate for the enzyme is added to measure, for example, the change of the absorbance caused by the color development based on the substrate decomposition. Thus, the antibody titer is calculated.

(Mammal)

The mammal is not specifically limited. However, the mammal is exemplified, for example, by human, mouse, rat, guinea pig, hamster, bovine, goat, sheep, pig, monkey, dog, and cat. Preferably, the mammal is human, mouse, rat, bovine, dog, and cat.

(DNA)

It is unnecessary for DNA in the second invention of the present invention to be fixed or immobilized to gold colloid unlike the conventional gene gun method and the particle gun method. Therefore, the preparation is extremely easy as compared with the conventional technique. Further, DNA may exist, for example, in sterile water and a sterile solvent as well as in a solvent to be used for a DNA immobilizing gold colloid solution as used in the conventional gene gun method or the like, provided that DNA exists stably and any harmful influence such as the destruction of cells into which DNA is to be introduced is not exerted. Further, it is also unnecessary to contain, for example, an excipient and an adjuvant unlike any DNA vaccine.

Further, as for DNA of the second invention of the present invention, the form thereof is not specifically limited, provided that DNA is designed so that DNA includes the region coding for the antigen for producing the antibody in the living body and DNA can express the predetermined antigen when DNA is introduced into the living body (into the cells) of the mammal.

For example, it is possible to exemplify that DNA is designed in a form in which DNA is included in an expression cassette or an expression vector. Further, for example, DNA may be arranged under the control of a promoter which is suitable for the introduction portion and the type of the mammal into which DNA is to be introduced. Further, it is also allowable to include one or a plurality of enhancer or enhancers in order to increase the amount of expression of the antigen.

The expression vector is not specifically limited, provided that the predetermined antigen is expressed when the expression vector is introduced into the living body (into the cells) of the mammal. For example, pcDNA3.1(−) plasmid vector or the like, which is a mammalian expression vector, is exemplified. The plasmid vector is known, which is available for those skilled in the art.

Further, the subcloning can be performed for the expression vector and the recombinant vector in accordance with any known method. In this procedure, the prokaryote host can be exemplified, for example, by *Escherichia coli, Bacillus subtilis*, and bacterial strain belonging to the genus *Pseudomonas*. In this case, as for the promoter, for example, it is possible to use tryptophan promoter, PL promoter, lac promoter, and tac promoter. As for the marker gene, for example, it is possible to use ampicillin resistance gene and tetracycline resistance gene. Further, the method for extracting the expression vector from host cells can follow any known method as well.

(Antigen)

DNA of the second invention of the present invention includes the region coding for the antigen to produce the antibody in the living body when DNA is introduced into the living body (into the cells) of the mammal.

The antigen of the second invention of the present invention includes the protein which includes such an amino acid sequence that one or several, for example, 1 to 10 and preferably 1 to 5 amino acid residue or residues of the amino acid sequence of the antigen is/are substituted, deleted, added, and/or inserted and which is functionally equivalent to the antigen, i.e., the protein which has the activity of the antigen. Further, it is allowable to use the entire amino acid sequence of the antigen. However, it is also allowable to use a portion (especially epitope) which is acknowledged to have the high antigenicity. Therefore, DNA described above also includes DNA which includes the region coding for the protein as described above. Further, it is also allowable to use a base sequence including no intron such as cDNA.

Note that it is known that the protein, which has an amino acid sequence modified by the deletion, the addition, and/or the substitution with any other amino acid, in relation to one or a plurality of amino acid residue or residues with respect to a certain amino acid sequence, maintains the biological activity.

The antigen is not specifically limited, provided that the antibody against the antigen is produced in the living body of the mammal when the antigen is introduced as DNA into the living body of the mammal. However, the antigen is preferably a tumor antigen.

In this case, the "tumor antigen" means such an antigen that the antigen is newly acquired, for example, except for the histocompatibility antigen and the organ/tissue specific antigen possessed by the mother cells in accordance with the canceration of the cells and the antigen is detected by an immunological method. The tumor antigen includes the tumor specific antigen (antigen which exists in only the tumor cells and which is not found in other normal cells) and the tumor associated antigen (antigen which exists in other organ/tissue or normal cells of different types/different lines and/or which is expressed in the course of development/differentiation).

The type of the tumor antigen of the second invention of the present invention is not specifically limited. However, the tumor antigen is preferably NY-ESO-1 antigen.

DNA, which codes for the NY-ESO-1 antigen, refers, for example, to DNA which codes for an amino acid sequence of human NY-ESO-1 antigen, in the case of human NY-ESO-1 antigen. Further, in the same manner as described above, DNA also includes DNA coding for the protein which includes such an amino acid sequence that one or several, for example, 1 to 10 and preferably 1 to 5 amino acid residue or residues of the amino acid sequence is/are substituted, deleted, added, and/or inserted and which is functionally equivalent to the human NY-ESO-1 antigen composed of the amino acid sequence, i.e., the protein which has the activity as the human NY-ESO-1 antigen.

Note that the antigen is preferably an antigen originating from an animal species into which DNA is to be introduced. For example, when the introduction is performed into human, it is preferable to use the human NY-ESO-1 antigen.

The introduction route of DNA is not specifically limited. However, it is preferable that the introduction route is parenteral. The introduction rout is exemplified, for example, by intravenous, intraarterial, subcutaneous, intradermal, intramuscular, or intraperitoneal route. Preferably, the introduction rout is subcutaneous route.

The introduction amount of DNA differs depending on, for example, the type and degree of disease, the distinction of sex, the age, the body weight of the mammal as well as the introduction route. However, the introduction amount of DNA is not specifically limited, provided that the effect of the second invention of the present invention is exhibited. The introduction amount of DNA is usually 0.001 μg to 1000 mg, preferably 0.01 μg to 10 mg, and more preferably 0.1 μg to 100 μg per one time of introduction.

DNA can be also used in combination with other medicines or drugs or the like. DNA may be administered simultaneously with other medicines or drugs or the like. Alternatively, DNA may be administered while providing an interval. However, any order of administration thereof is available without causing any problem.

(DNA Vaccine)

DNA of the second invention of the present invention can be in a form of vaccine, i.e., DNA vaccine by appropriately adopting a known method for forming the vaccine.

In this case, DNA can be blended with, for example, a carrier which is permittable in view of the formation of pharmaceutical preparation (for example, isotonic solution containing physiological saline, glucose, and other adjunct agent as exemplified, for example, by D-sorbitol, D-mannose, D-mannitol, and sodium chloride, and appropriate dissolution auxiliary agent, for example, alcohol, specifically ethanol, polyalcohol, for example, propylene glycol and polyethylene glycol, and nonionic surfactant, for example, Polysorbate 80™ and HCO-50 can be exemplified, but there is no limitation thereto), an appropriate excipient, and an adjuvant so that DNA may be formed into a pharmaceutical preparation to be capable of being used.

Further, the DNA vaccine may contain a pharmaceutically permittable carrier in order to prepare the excipient or the carrier which is permittable in view of the formation of pharmaceutical preparation. It is also allowable to contain a biocompatible material including, for example, silicone, collagen, and gelatin.

Further, it is also allowable to use an emulsion containing various adjuvants. A variety of adjuvants are known, and those skilled in the art can easily select appropriate one. Further, in addition to the adjuvant described above, it is also allowable to contain one or two or more additives for pharmaceutical preparation selected, for example, from diluent, perfume, antiseptic or preservative, excipient, disintegrator, lubricant, binder, emulsifier, and plasticizer.

The introduction amount of the DNA vaccine differs depending on, for example, the type and degree of disease, the distinction of sex, the age, the body weight of the mammal as well as the introduction route. However, the introduction amount of the DNA vaccine is not specifically limited, provided that the effect of the second invention of the present invention is exhibited. The amount of DNA is usually 0.001 μg to 1000 mg, preferably 0.01 μg to 10 mg, and more preferably 0.1 μg to 100 μg per one time of introduction.

The DNA vaccine can be also used in combination with other medicines or drugs or vaccine. The DNA vaccine may be administered simultaneously with other medicines or drugs or the like. Alternatively, the DNA vaccine may be administered while providing an interval. However, any order of administration thereof is available without causing any problem.

EXAMPLES

The present invention will be explained below more specifically with reference to Examples. However, the present invention is not limited to Examples described below without deviating from the gist or essential characteristics thereof.

(Production of Plasmid DNA)

cDNA of human NY-ESO-1 gene was purchased from Origene (Cat #: SC303002), and the gene sequence was subcloned into pcDNA3.1(−) (Life Technologies) in accordance with a known method.

(Tumor Cells)

CT26 cells, which stably expressed human NY-ESO-1 protein, were used as the tumor cells used for the tumor transplantation described later on.

The cells were prepared in accordance with the following procedure. Cultured mouse colorectal cancer cell CT26 cell strain was washed with PBS, followed by being exfoliated with PBS containing 0.5% trypsin and recovered with RPMI1640 medium containing 10% FBS. After the centrifugation (1200 rpm, 5 minutes, 4° C.), the supernatant was removed. Cells were washed twice with OPTI-MEM medium and cultured overnight with OPTI-MEM medium. On the following day, human NY-ESO-1 gene-incorporated plasmid was introduced by using Lipofectamine 2000 Transfection Reagent (Life Technologies), followed by being cultured. Gene-introduced CT26 cells were exfoliated and recovered by means of the trypsin treatment. Cells were cultured for 10 days with RPMI1640 medium containing 10% FBS containing 350 μg/ml G418, and then the monocloning was performed by means of the limiting dilution. Established human NY-ESO-1 protein-stably expressing CT26 cells were cultured with RPMI1640 medium containing 10% FBS.

Example 1

(Evaluation of Discharge Force of Needleless Injector)

35 μL of DNA solution (solvent: PBS, final concentration: 1 μg/μL) was charged into the needleless injector shown in FIG. 1 (nozzle diameter: diameter 0.1 mm) to evaluate the pressure (discharge force) in the injector ranging from the pressurization of the DNA solution brought about by the combustion of the igniter powder to the state provided after the discharge. 35 mg of a propellant (ZPP) containing zirconium and potassium perchlorate was used as the propellant.

The discharge force was measured by means of the following method like a measuring method described in Japanese Patent Application Laid-Open No. 2005-21640.

That is, the force of discharge was applied in a dispersed manner to a diaphragm of a load cell arranged downstream from the nozzle. The output from the load cell was sampled or collected by a data collecting and displaying device via a detection amplifier, and the output was displayed and stored as the discharge force (N) in the course of time.

Figure 2:
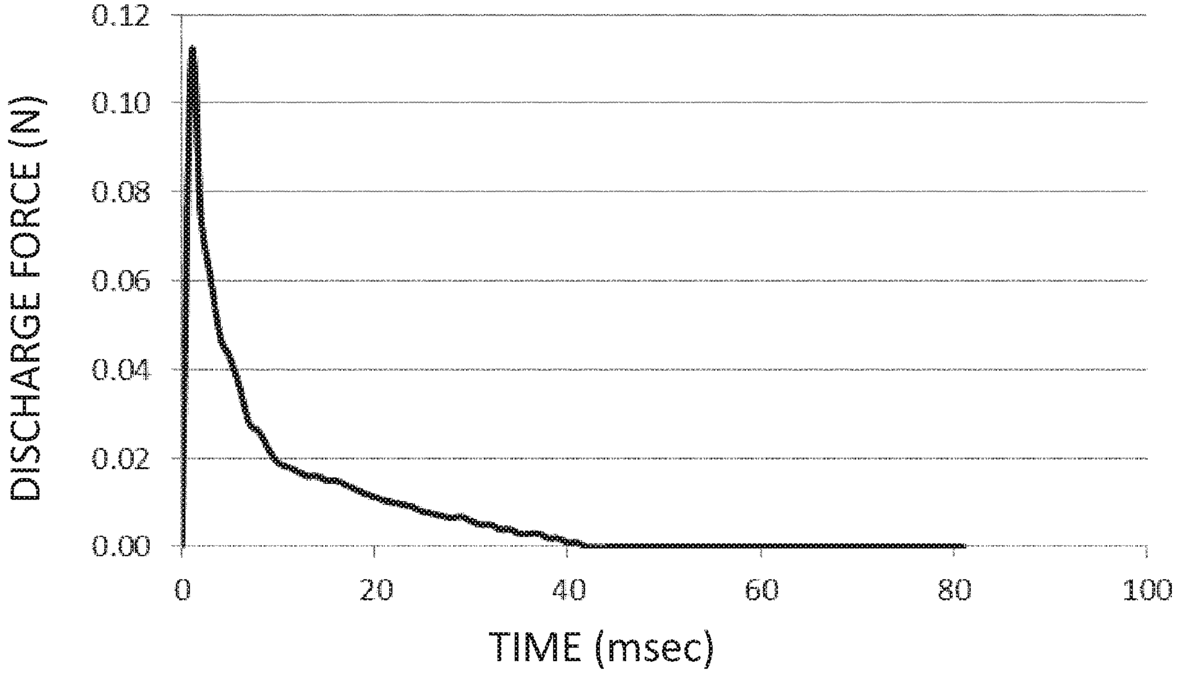
FIG. 2 shows a graph illustrating the time course of the discharge force of a DNA solution in an embodiment of the second invention of the present invention.

FIG. 2 shows a graph illustrating the time course of the discharge force of the DNA solution. It was revealed that the pressure returns to the pressure provided before the pressurization, in an extremely short period of time after the pressure, which was applied to the DNA solution, reached the initial peak discharge force.

Antitumor Test

Example 2-1 (Needleless Injector)

35 μL of the DNA solution (solvent: PBS, final concentration: 1 μg/μL) was charged into the needleless injector used in Example 1 described above, and the injection was performed into a hair shaved right back portion of female BALB/c mouse (8 weeks old, Japan SLC). The day of the first administration was designated as the 0th day, and the second administration was performed on the 8th day.

On the 16th day, mouse colorectal cancer cell CT26 cell strain stably introduced with NY-EXO-1 gene cultured in T75 flask (Nunc) was washed with PBS. After that, cells were exfoliated with PBS containing 0.5% trypsin, and cells were recovered with 8 ml of RPMI1640 medium containing 10% FBS. After the centrifugation (1200 rpm, 5 minutes, 4° C.), the supernatant was removed. Cells were washed twice with RPMI1640 medium, and cells were resuspended in RPMI1640 medium at a concentration of $1\times10^6$ cells/100 μL. Subcutaneous transplantation was performed in an amount of 100 μL/individual to a hair shaved right abdomen portion of female BALB/c mouse.

After the transplantation, the size of transplanted tumor (long diameter (major axis) and short diameter (minor axis)) was measured in a time-dependent manner by using an electronic caliper. Note that the experiment was carried out independently with six individuals in Example 2-1.

Comparative Example 2-1 (Needle-Equipped Injection)

An experiment was carried out in the same manner as Example 2-1 except that a needle-equipped injector was used for the injection. Note that the experiment was carried out independently with five individuals in Comparative Example 2-1.

Comparative Example 2-2 (Conventional Gene Gun)

An experiment was carried out in the same manner as Example 2-1 except that a gene gun (Helios Gene Gun System (Bio-Rad)) was used for the injection. Note that the gas pressure during the injection was 350 to 400 pound-force per square inch (p.s.i). Plasmid DNA was administered in an amount of 1 μg/mouse in a form of being coated with 1 μm gold particles (Bio-Rad). Further, the experiment was carried out independently with four individuals in Comparative Example 2-2.

Comparative Example 2-3 (Untreated)

An experiment was carried out in the same manner as Example 2-1 except that the injection was not carried out. Note that the experiment was carried out independently with four individuals in Comparative Example 2-3.

Figure 3A:
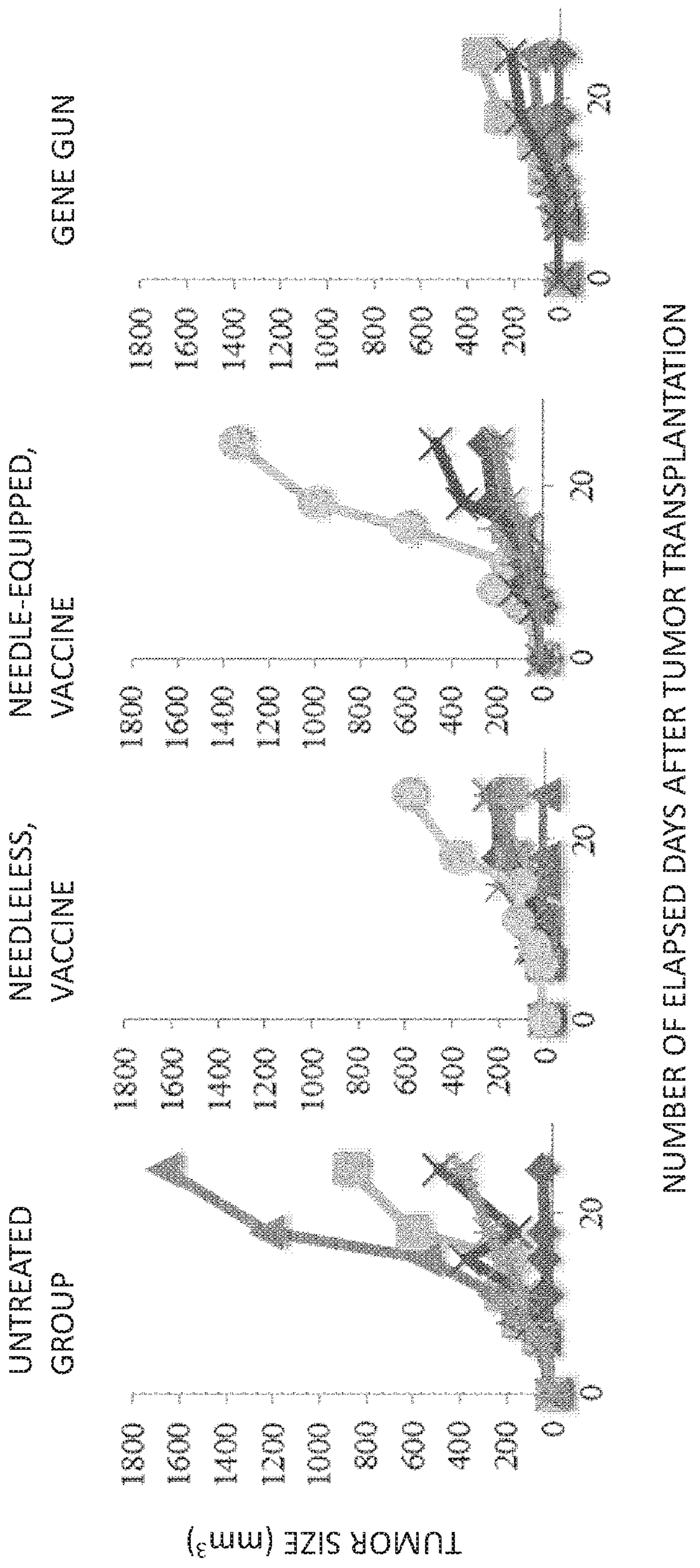
FIG. 3A shows graphs illustrating the relationship between the tumor size and the number of elapsed days after the transplantation of tumor in an embodiment of the second invention of the present invention.
Figure 3B:
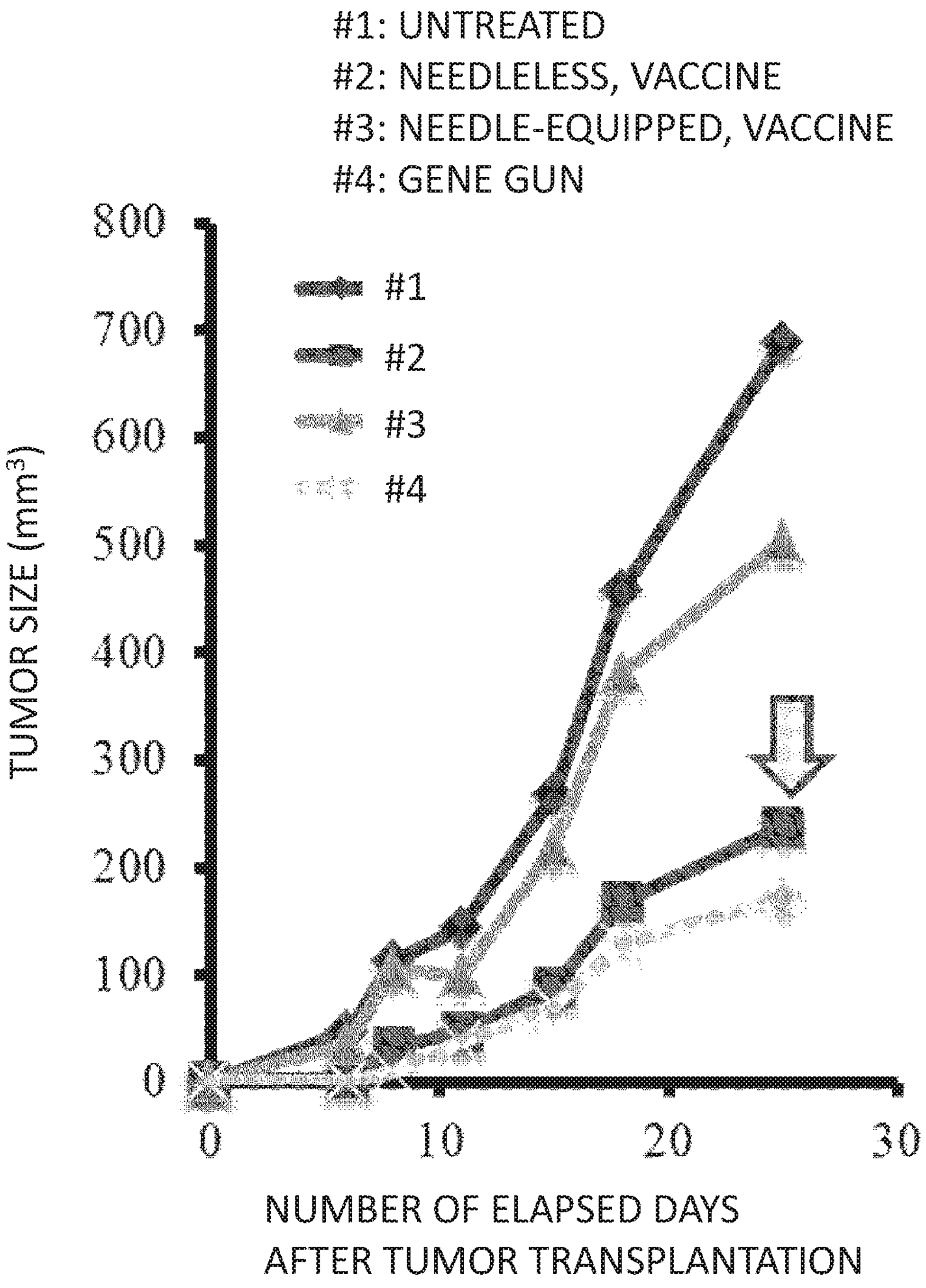
FIG. 3B shows a graph illustrating the relationship between the tumor size and the number of elapsed days after the transplantation of tumor in an embodiment of the second invention of the present invention.

FIG. 3A shows graphs illustrating the change of the tumor size measured in the time-dependent manner in relation to the respective individuals of the respective examples. Further, FIG. 3B shows a graph illustrating the change of the average value of the tumor size in the respective examples.

According to the results, it has been revealed that in the case of the needleless injection, the increase of tumor is not suppressed as compared with the case of the use of the conventional gene gun, but the increase of tumor is remarkably suppressed as compared with the cases of the untreated group and the needle-equipped injection.

Antibody Titer Measurement Test 1

Example 3-1 (Needleless Injection)

35 μL of DNA solution (solvent: PBS, final concentration: 1 μg/μL) was charged into the needleless injector used in Example 1 described above, and the injection was performed into a hair shaved right back portion of female BALB/c mouse (8 weeks old, Japan SLC). The day of the first administration was designated as the 0th day, and the second administration was performed on the 8th day.

On the 16th day, blood was collected from mouse, followed by being stationarily placed overnight at 4° C. After that, the centrifugation (10000 rpm, 5 minutes) was performed to separate and obtain serum.

The antibody titer of anti-human NY-ESO-1 antibody (pan-IgG) existing in the obtained serum was measured by means of the ELISA method. Note that the experiment was carried out independently with six individuals in Example 3-1.

The concentration of NY-ESO-1 protein (Origene, Cat #TP313318) was adjusted to 0.4 ng/ml, and NY-ESO-1 protein was added to 96-well flat bottom MaxiSorp plate (Nunc) in an amount of 50 μl/well, followed by being stationarily placed overnight at 4° C. The antibody solution was removed by means of decantation, followed by being washed four times with washing buffer (PBS containing 0.05% Tween 20). Blocking buffer (PBS containing 1% BSA) was added in an amount of 200 μl/well, followed by being stationarily placed for 1 hour at room temperature. Sample serum was diluted with blocking buffer in a stepwise manner. Blocking buffer was discarded by means of decantation, and diluted serum or blocking buffer (blank well) was added in an amount of 100 μl/well, followed by being stationarily placed for 2 hours at room temperature. Diluted serum was discarded by means of decantation, followed by being washed with washing buffer four times. HRP-labeled anti-mouse IgG antibody was diluted 5000 times with blocking buffer, which was added in an amount of 100 μl/well, followed by being stationarily placed for 1 hour at room temperature. The antibody solution was discharged by means of decantation, followed by being washed with washing buffer four times. After completely removing washing buffer, TMB solution was added in an amount of 100 μl/well. After being stationarily placed for 3 minutes at room temperature, 0.18 M sulfuric acid was added in an amount of 100 μl/well to measure the absorbance at 450 nm by means of Microplate Reader Model 680 (Bio-rad). The numerical value, which was obtained by subtracting the value of blank well from the value of each well, was used as the value of each well to perform the data analysis. Duplicate was prepared for each sample.

Comparative Example 3-1 (Needle-Equipped Injection)

An experiment was carried out in the same manner as Example 3-1 except that a needle-equipped injector was used for the injection. Note that the experiment was carried out independently with five individuals in Comparative Example 3-1.

Comparative Example 3-2 (Conventional Gene Gun)

An experiment was carried out in the same manner as Example 3-1 except that a gene gun (Helios Gene Gun System (Bio-Rad)) was used for the injection. Note that the gas pressure during the injection was 350 to 400 p.s.i. Plasmid DNA was administered in an amount of 1 μg/mouse in a form of being coated with 1 m gold particles (Bio-Rad). Further, the experiment was carried out independently with four individuals in Comparative Example 3-2.

Comparative Example 3-3 (Untreated)

An experiment was carried out in the same manner as Example 3-1 except that the injection was not carried out. Note that the experiment was carried out independently with four individuals in Comparative Example 3-3.

Figure 4A:
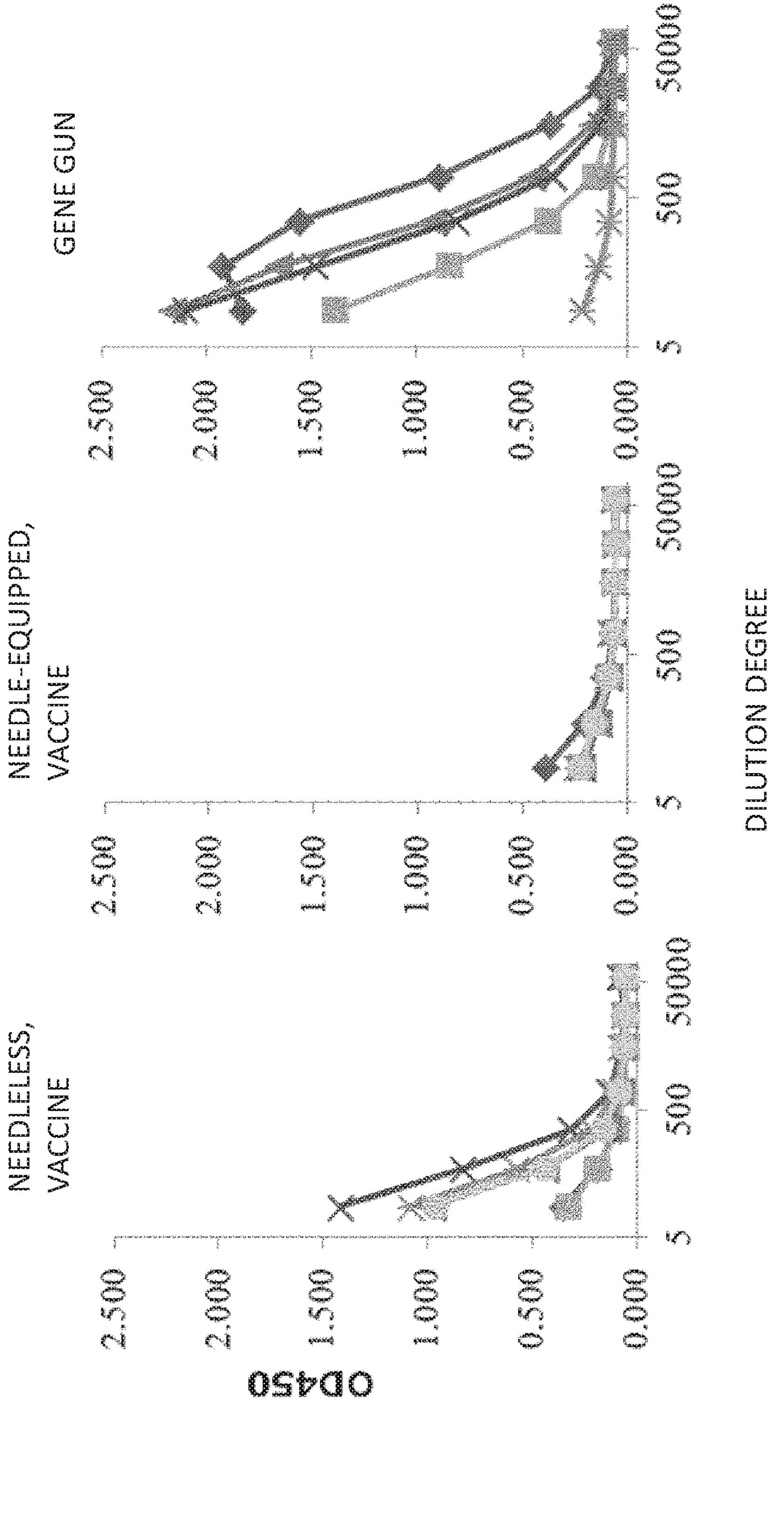
FIG. 4A shows graphs illustrating the relationship between the dilution degree and the absorbance at 450 nm (OD450) in an embodiment of the second invention of the present invention.
Figure 4B:
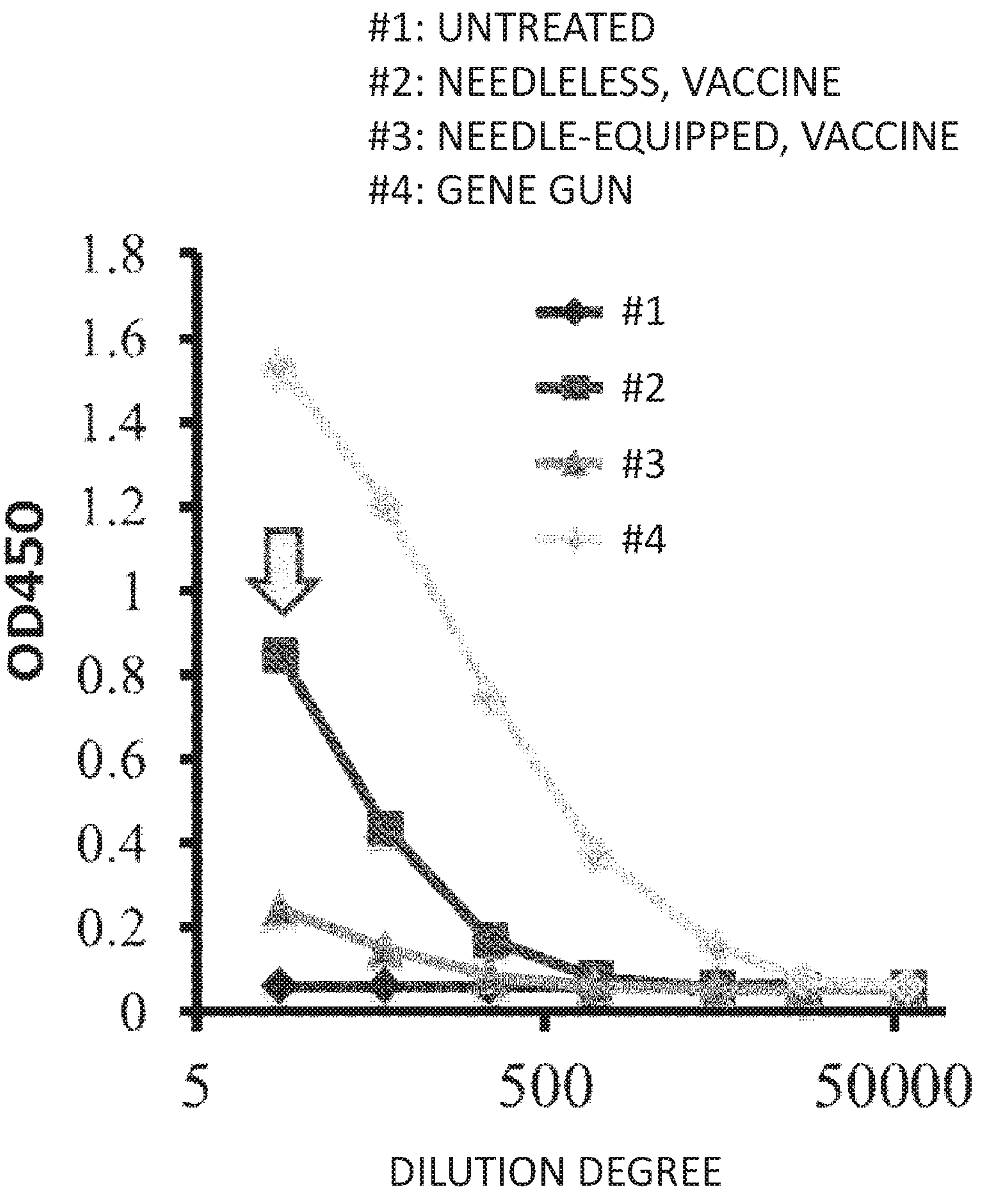
FIG. 4B shows a graph illustrating the relationship between the dilution degree and the absorbance at 450 nm (OD450) in an embodiment of the second invention of the present invention.

FIG. 4A shows graphs illustrating the relationship between the dilution degree and the value of OD450 in relation to the respective individuals of the respective examples. Further, FIG. 4B shows a graph illustrating the relationship between the dilution degree and the average value of OD450 in the respective examples.

According to the results, it has been revealed that in the case of the needleless injection, any large antibody titer is not exhibited as compared with the case of the use of the conventional gene gun, but the antibody titer, which is remarkably larger than those obtained in the cases of the untreated group and the needle-equipped injection, is exhibited.

Antibody Titer Measurement Test 2

Example 4-1, Comparative Examples 4-1 to 4-3

An experiment was carried out in the same manner as Example 3-1 except that the antibody to be measured by the ELISA method was anti-human NY-ESO-1 antibody (IgG1), which was designated as Example 4-1 (needleless injection).

Similarly, experiments were carried out in the same manner as Comparative Example 3-1, Comparative Example 3-2, and Comparative Example 3-3 except that the antibody to be measured by the ELISA method was anti-human NY-ESO-1 antibody (IgG1), which were designated as Comparative Example 4-1 (needle-equipped injection), Comparative Example 4-2 (conventional gene gun), and Comparative Example 4-3 (untreated) respectively.

Figure 5A:
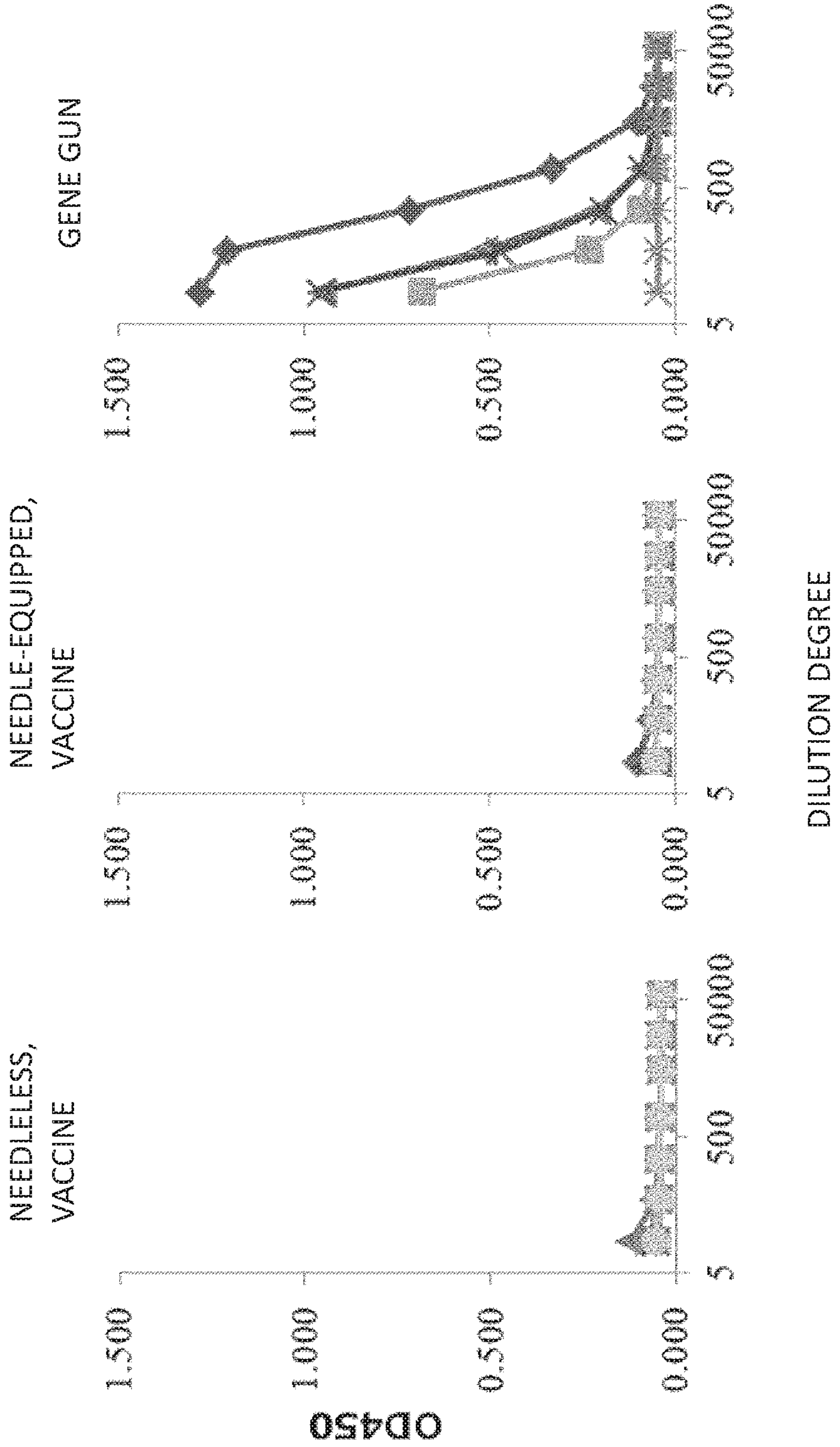
FIG. 5A shows graphs illustrating the relationship between the dilution degree and the absorbance at 450 nm (OD450) in an embodiment of the second invention of the present invention.
Figure 5B:
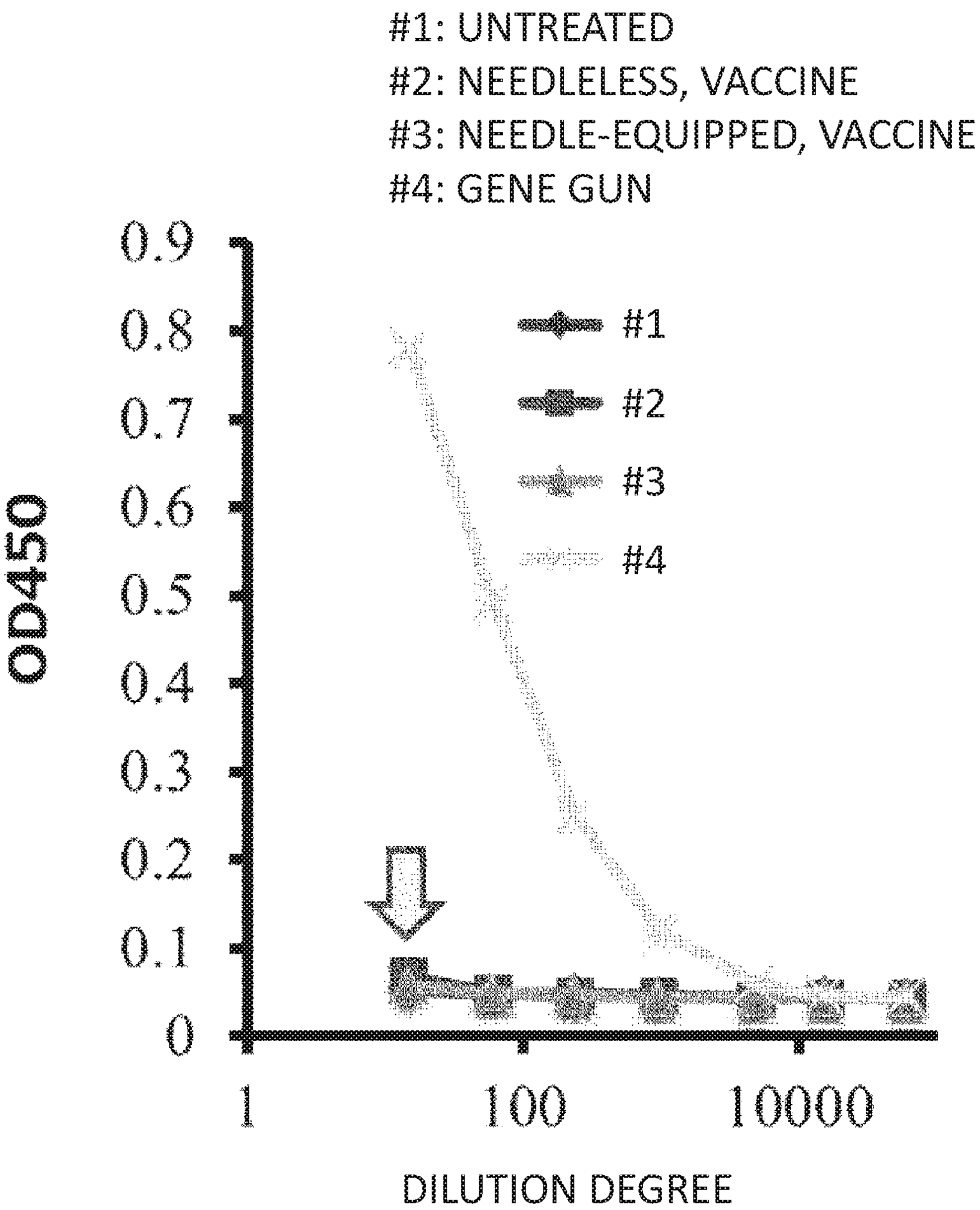
FIG. 5B shows a graph illustrating the relationship between the dilution degree and the absorbance at 450 nm (OD450) in an embodiment of the second invention of the present invention.

FIG. 5A shows graphs illustrating the relationship between the dilution degree and the value of OD450 in relation to the respective individuals of the respective examples. Further, FIG. 5B shows a graph illustrating the relationship between the dilution degree and the average value of OD450 in the respective examples.

According to the results, it has been revealed that in the case of the use of the conventional gene gun, the large antibody titer is exhibited, but any large antibody titer is not exhibited in the case of the needleless injection in the same manner as the case of the untreated group.

Antibody Titer Measurement Test 3

Example 5-1, Comparative Examples 5-1 to 5-3

An experiment was carried out in the same manner as Example 3-1 except that the antibody to be measured by the ELISA method was anti-human NY-ESO-1 antibody (IgG2a), which was designated as Example 5-1 (needleless injection).

Similarly, experiments were carried out in the same manner as Comparative Example 3-1, Comparative Example 3-2, and Comparative Example 3-3 except that the antibody to be measured by the ELISA method was anti-human NY-ESO-1 antibody (IgG2a), which were designated as Comparative Example 5-1 (needle-equipped injection), Comparative Example 5-2 (conventional gene gun), and Comparative Example 5-3 (untreated) respectively.

Figure 6A:
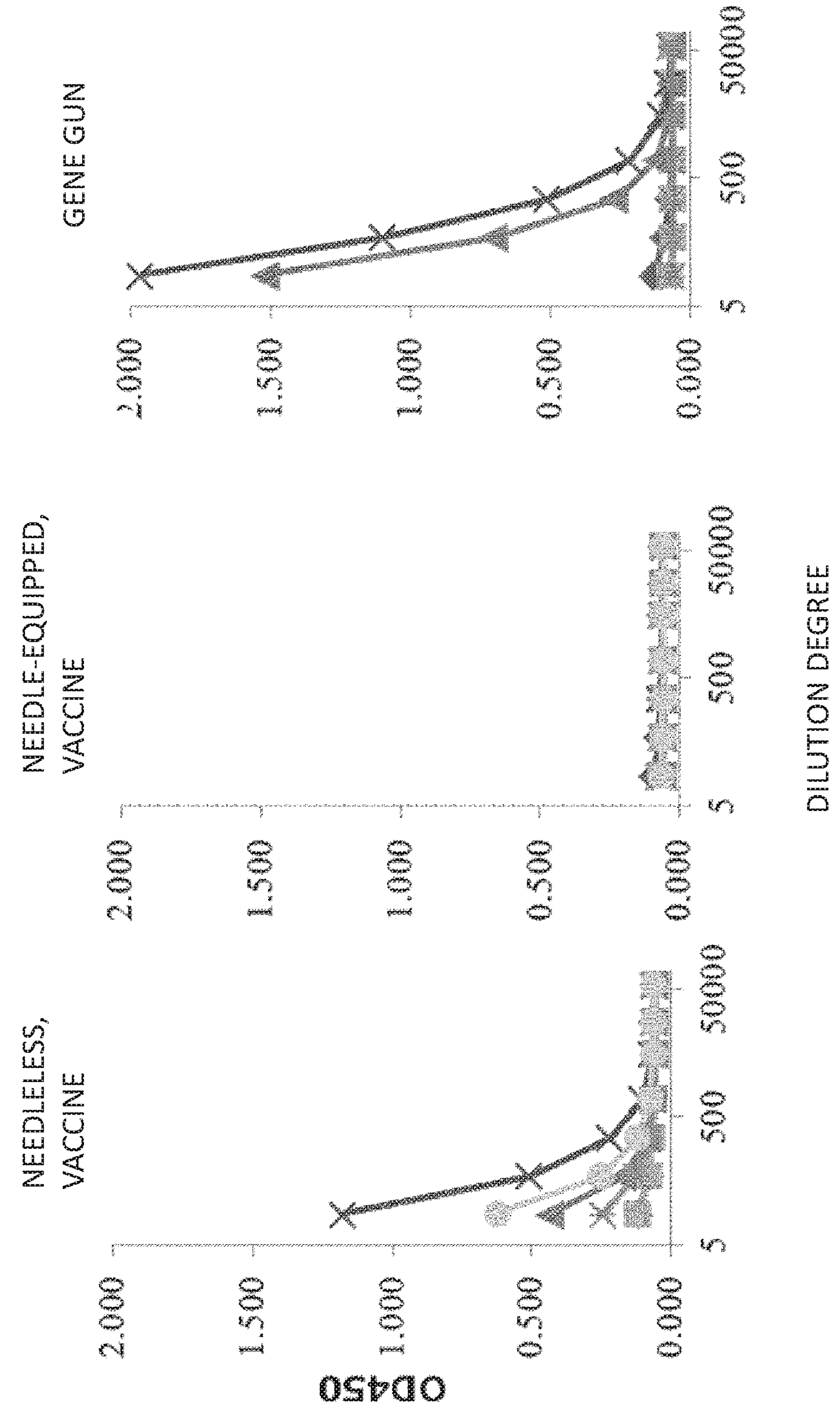
FIG. 6A shows graphs illustrating the relationship between the dilution degree and the absorbance at 450 nm (OD450) in an embodiment of the second invention of the present invention.
Figure 6B:
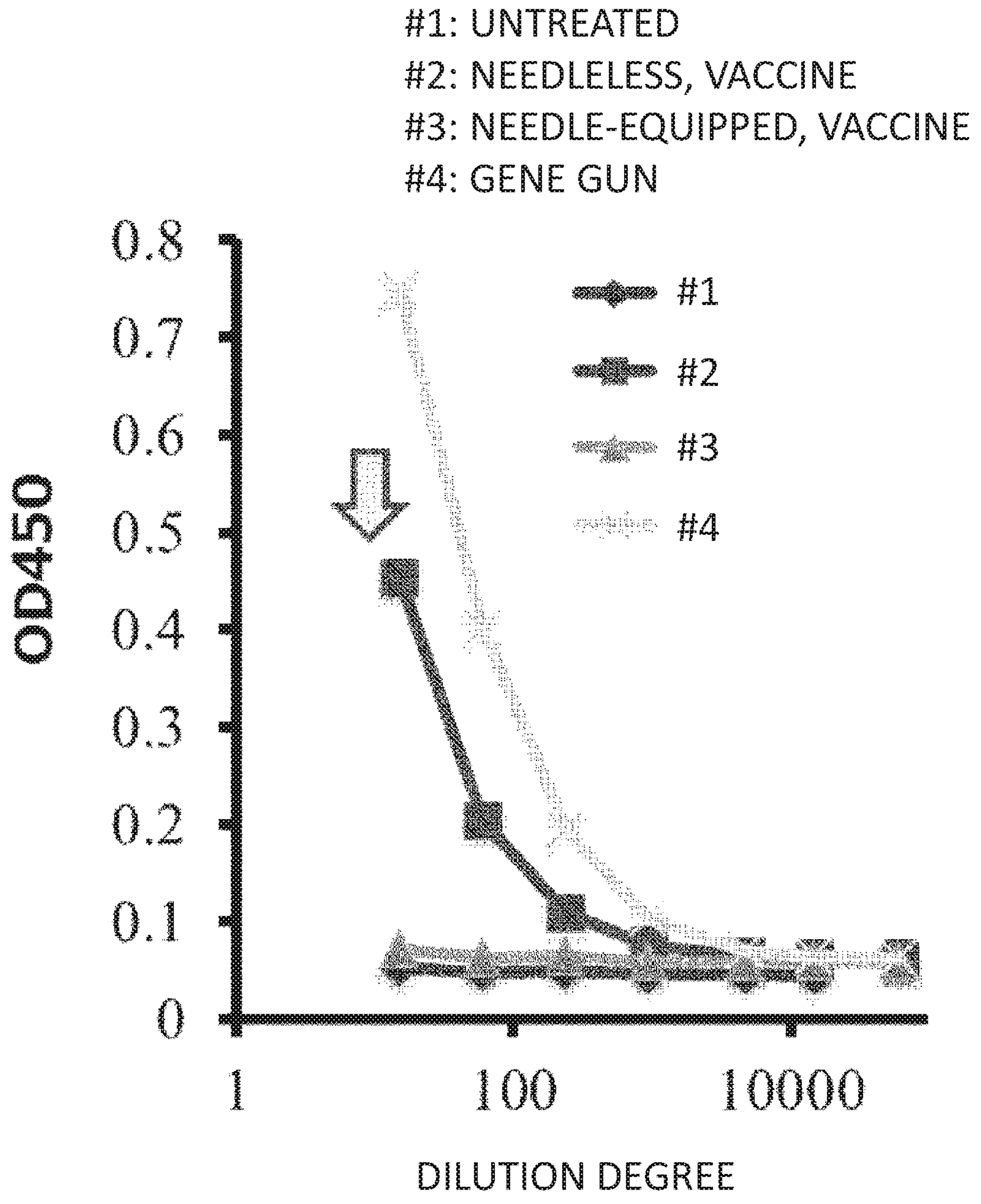
FIG. 6B shows a graph illustrating the relationship between the dilution degree and the absorbance at 450 nm (OD450) in an embodiment of the second invention of the present invention.

FIG. 6A shows graphs illustrating the relationship between the dilution degree and the value of OD450 in relation to the respective individuals of the respective examples. Further, FIG. 6B shows a graph illustrating the relationship between the dilution degree and the average value of OD450 in the respective examples.

According to the results, it has been revealed that in the case of the needleless injection, any large antibody titer is not exhibited as compared with the case of the use of the conventional gene gun, but the antibody titer, which is remarkably larger than those obtained in the cases of the untreated group and the needle-equipped injection, is exhibited.

DESCRIPTION OF THE REFERENCE SIGNS

1: injector, 2: housing, 3: syringe unit, 4: plunger, 5: piston, 6: main injector body, 7: driving unit, 8: button, 9: battery, 10: injector assembly, 31: nozzle unit, 31*a*: injection port, 32: charging chamber, 71: igniter.

The invention claimed is:

1. A method for injecting a DNA solution, the method comprising:

introducing DNA, in a form of vaccine, including a region coding for an antigen into a living body of a mammal by using a needleless injector to inject the DNA solution into an injection target area without using any injection needle such that Type 1 helper T cells are more superiorly activated than Type 2 helper T cells in the living body of the mammal, the needleless injector comprising:

an accommodating unit which accommodates the DNA solution, an ignition device including an igniter powder which exhibits such a pressure characteristic that a plasma is generated during combustion immediately after ignition and then a generated pressure is lowered when a temperature becomes ordinary temperature and a combustion product is condensed on account of no gas component which is contained in the combustion product or any gas component which is contained in the combustion product and an amount of the gas component in the condensed combustion product is decreased as compared with that provided before the condensation, and a nozzle unit having a discharge port through which the DNA solution pressurized by the combustion of the igniter powder in the ignition device flows so that the DNA solution is discharged to the injection target area, wherein:

a temperature of the combustion product, which is provided during the pressurization, changes to a neighborhood of the ordinary temperature within 20 msec after a pressure, which is applied to the DNA solution on account of the combustion of the igniter powder, reaches an initial peak discharge force during a pressurization process for discharging the DNA solution.

2. The method according to claim 1, wherein the mammal is a mouse.

3. The method according to claim 1, wherein the antigen is NY-ESO-1 antigen.

4. The method according to claim 1, wherein the Type 1 helper T cells are configured to produce an IgG2 antibody, wherein the Type 2 helper T cells are configured to produce an IgG1 antibody, and wherein the IgG2 antibody is detected and the IgG1 antibody is not detected in the living body of the mammal when the Type 1 helper T cells are more superiorly activated than the Type 2 helper T cells in the living body of the mammal.

5. The method according to claim 1, wherein the Type 1 helper T cells are configured to produce an IgG2 antibody, wherein the Type 2 helper T cells are configured to produce an IgG1 antibody, and wherein the IgG2 antibody is detected and an ineffective amount of IgG1 antibody is detected in the living body of the mammal when the Type 1 helper T cells are more superiorly activated than the Type 2 helper T cells in the living body of the mammal.

6. The method according to claim 1, wherein an amount of the DNA being introduced is in a range of 0.001 μg to 1000 mg.

7. The method according to claim 1, further comprising prior to introducing the DNA, blending the DNA with a carrier which is permittable in view of formation of pharmaceutical preparation, an appropriate excipient, and an adjuvant.

* * * * *